(12) United States Patent
Kiefer et al.

(10) Patent No.: US 6,939,951 B1
(45) Date of Patent: Sep. 6, 2005

(54) REFOLDING OF MEMBRANE PROTEINS

(75) Inventors: Hans Kiefer, Stuttgart (DE); Klaus Maier, Stuttgart (DE)

(73) Assignee: M-Phasys GmbH, Tubingen (DE)

( * ) Notice: Subject to any disclaimer, the term of this patent is extended or adjusted under 35 U.S.C. 154(b) by 412 days.

(21) Appl. No.: 10/069,433

(22) PCT Filed: Aug. 10, 2000

(86) PCT No.: PCT/EP00/07763

§ 371 (c)(1),
(2), (4) Date: May 31, 2002

(87) PCT Pub. No.: WO01/14407

PCT Pub. Date: Mar. 1, 2001

(30) Foreign Application Priority Data

Aug. 19, 1999 (DE) ................................ 199 39 246

(51) Int. Cl.[7] ............................................... C07K 1/02
(52) U.S. Cl. ....................................................... 530/350
(58) Field of Search ......................................... 530/350

(56) References Cited

FOREIGN PATENT DOCUMENTS

| DE | 3014189 | 10/1981 |
| --- | --- | --- |
| EP | 0321606 | 6/1989 |
| EP | 0334278 | 9/1989 |
| WO | WO 94/00557 | 1/1994 |
| WO | WO 95/03069 | 2/1995 |
| WO | WO 98/19789 | 5/1998 |

OTHER PUBLICATIONS

Nekrasova et al. "Overexpression, solubilization and purification of rat and human olfactory receptors" Eur. J. Biochem. (1996) 238: 28-37.*

Kiefer, H., et al. (1996) Expression of an Olfactory Receptor in *Escherichia coli*: Purification, Reconstitution, and Ligand Binding. Biochemistry 35:10677-16084.

Kiefer, H., et al. (1999) Refolding of G protein-coupled receptors from inclusion bodies produced in *E. coli*. Biochemical Society Transactions p A141.

Kiefer, H., et al. (1999) Refolding of G-protein-coupled receptors from inclusion bodies produced in *Escherichia coli*. Biochemical Society Transactions 27(6):908-912.

Rogl, H., et al. (1998) Refolding of *Escherichia coli* produced membrane protein inclusion bodies immobilised by nickel chelating chromatography. FEBS Letters 432:21-26.

Tandon, S. and Horowitz, P. M. (1987) Detergent-assisted Refolding of Guanidinium Chloride-denatured Rhodanese. J. Biol. Chem. 262(10):4486-4491.

Zardeneta, G. and Horowitz, P. M. (1992) Micelle-assisted Protein Folding. J. Biol. Chem. 267(9):5811-5816.

Ikematsu et al., "Direct reconstitution of bacteriorhodopsin into planar phospholipid bilayers—detergent effect, "*Biophysical Chemistry*, vol. 54, (1995), pp. 155-164.

Neugebauer, J., "Detergents: an Overview,"*Methods in Enzymology*, vol. 182 (1990), pp. 239-253.

Cerione et al., (1984) "The Mammalian $\beta_2$-Adrenergic Receptor: Reconstitution of Functional Interactions between Pure Receptor and Pure Stimulatory Nucleotide Binding Protein of the Adenylate Cyclase System,"*Biochemistry*, vol. 23, pp. 4519-4525.

* cited by examiner

*Primary Examiner*—Jean C. Witz
*Assistant Examiner*—Susan Hanley
(74) *Attorney, Agent, or Firm*—Knobbe, Martens, Olson & Bear, LLP

(57) ABSTRACT

In a method for production of membrane proteins or receptors folded into their native structure, first, proteins solubilized in a first detergent are provided. To induce folding of proteins into their native form, the first detergent is exchanged for a second detergent. Both for the first and for the second detergent, examples are shown.

19 Claims, No Drawings

REFOLDING OF MEMBRANE PROTEINS

This is the U.S. National Phase under 35 U.S.C. §371 of International Application PCT/EP00/07763, filed Aug. 10, 2000, which claims priority to German Application 19939246.3, filed Aug. 19, 1999.

FIELD OF THE INVENTION

The present invention relates to a method for the production of proteins folded into their native or active structure, said protein being from the group comprising membrane proteins, in particular receptors, preferably from the family of G-protein-coupled receptors, as well as partial sequences, homologous sequences, mutated sequences and derived sequences of membrane proteins and receptors, with the steps:
Providing of protein solubilized in a first detergent, and
Exchange of said first detergent for a second detergent, which induces the folding of protein into its native or active form.

BACKGROUND OF THE INVENTION

For membrane proteins, such a method is known from the article "Refolding of *Escherichia coli* produced membrane protein inclusion bodies immobilised by nickel chelating chromatography", Rogl et al. in FEBS Letters 432 (1998) 21–26.

A method for refolding of receptor protein is known from the article "Expression of an Olfactory Receptor in *Escherichia coli*: Purification, Reconstitution, and Ligand Binding" by Kiefer et al. in Biochemistry 35 (1996) 16077–16084.

Both publications are based on the problem that membrane proteins, to which receptors also belong, can be produced in large quantities with the help of expression vectors in bacteria, but that the protein produced, however, is not active. The protein is, namely, not integrated into the membrane, but, first, is present in a denatured state and has to be refolded into the native or active structure. The aggregates of "inactive" protein are designated in English literature as inclusion bodies.

For the membrane proteins Toc75 and LHCP, Rogl et al. describe a method in which N-Lauroylsarcosine is used as first detergent and Triton X-100® is used as second detergent. By exchanging the chaotrope for the mild detergent, refolding of the aggregated protein was induced.

According to Kiefer et al., a G-protein-coupled olfactory receptor was transformed into the active structure during the binding onto a nickel column by detergent exchange from N-Lauroylsarcosine to digitonin.

In both cases, it could be shown that the aggregated protein first existing in the form of inclusion bodies was, first, solubilized in a denaturing detergent and, then, by the detergent exchange described, transformed into its active structure, which was verified by corresponding binding measurements.

There is a great scientific and commercial interest in membrane proteins, in particular in receptors in native or active form, since membrane proteins are components of all biological membranes and impart to the specificity of different cellular membranes, they are particularly responsible for the exchange of substances and signals.

The specific recognition of a chemical compound by the corresponding receptor has e.g. the consequence that the target cell changes its physiological state. That is why receptors are the most important target molecules for drugs, approximately ¾ of all commercially available pharmaceuticals act on receptors, most of which, again, act on so-called G-protein-coupled receptors, which have in the human genome several hundreds of representatives.

For the development of specific antibodies, of drugs etc. it is, in view of the above, most desirable to have membrane proteins, in particular receptors in active or native structure available in large quantities. Since these proteins occur, in tissue, only in very small concentrations, it is necessary to use a system for recombinant over-expression of membrane proteins and receptors. For this purpose, on the one hand, in eukaryotic cells (cells of mammals or insects), functional protein can be produced, however, the systems are expensive, and the expression rates are low, which is also disadvantageous. Functional protein can be obtained via bacterial expression as well, the expression rate, however, is even lower than in eukaryotic expression.

In view of the above, the two publications mentioned at the outset describe methods, in which the protein is expressed in the inner part of the cell, where it, however, aggregates, and hence is not functionally available. The advantage of this method is that very large quantities of protein can be produced, Kiefer et al. report that up to 10% of cell protein and, thus, 100–10,000 times more protein than with other expression systems can be produced. The inclusion bodies produced in that way, which Rogl et al. have also reported about, must then first of all, be solubilized and, via the exchange of detergents already described at the outset, be transformed into their native or active structure.

Of course, commercial interest is not only directed to membrane proteins and receptors in their naturally existing sequence, rather, also partial sequences, homologous sequences, mutated sequences or derived sequences of membrane proteins and receptors are an object of this invention, as they allow, depending on functionality, not only insights into the structure of membrane proteins and receptors, but also a rational drug design.

In this context it should be mentioned that the DNA sequence of many receptors is known, such sequences are contained in the EMBL database. As these DNA sequences, in most cases, do not contain introns, the coding sequence can be produced by PCR from genomic DNA or by RT-PCR from mRNA. This DNA can then be cloned into a corresponding expression vector.

However, the structure of the translation product is unknown, so that providing proteins which are an object of the invention in sufficient quantity allows crystallization experiments etc. to further elucidate the structure.

It should also be mentioned that receptors expressed in eukaryotic and in bacteria can be distinguished by glycosylation. G-protein-coupled receptors, namely, possess on the N-terminus one or more glycosylation sites, which are modified in the endoplasmic reticulum or later in the Golgi apparatus with an oligosaccharide. Bacteria, in contrast, do not modify these sequences.

By treating a portion of the protein with N-glycosidase F or N-glycosidase A, the saccharide can be cleaved off, so that on an SDS gel a different extend of migration of the protein can be distinguished before and after this treatment, if the protein was expressed in eukaryotic cells. For bacterially expressed protein, no differences in the extend of migration can be distinguished.

Although the methods for the production of membrane protein or receptor protein that are described in the publications mentioned above lead to active structures, the methods described, according to the knowledge of the inventors of the present application here submitted, are insofar not satisfying, as the yield is low and the method is poorly reproducible.

SUMMARY OF THE INVENTION

In view of the above, it is an object of the present invention to improve the method mentioned above to reach—with good reproducibility—a high yield of the protein in active or native structure.

According to the invention, this object is achieved by selecting the second detergent from the group:

Alkyl-N,N-dimethylglycine (alkyl=C8–C16)

Alkylglycosides (alkyl=C5–C12, also branched-chained or cyclic alkyl rests, glycoside=all mono- and disaccharides)

Saccharide fatty acid ester (e.g. sucrosemonododecanoate)

Alkylthioglycosides (alkyl=C5–C12, also branched-chained or cyclic alkyl rests, glycoside=all mono- and disaccharides with S- instead of O-glycosidic bond)

Bile acids (cholate, deoxycholate) and derivatives (e.g. CHAPS, CHAPSO)

Glucamides (MEGA-8 to -10, HEGA)

Lecithins and lysolecithins (e.g. DHPC, C12-lysolecithin)

Alkyl-Phosphorylcholine (Alkyl=C10–C16).

The object underlying the invention is in that way completely achieved.

DETAILED DESCRIPTION OF THE PREFERRED EMBODIMENT

The inventors of the submitted application have, namely, recognized that the low yield and the lacking reproducibility in the known methods is to be assigned to the second detergent. Surprisingly, the yields were, namely, distinctively higher and the results were more reproducible, if the second detergent was selected from the group mentioned above. Further, it has to be taken care that the second detergent, in its final concentration, is above the critical micellar concentration. This cmc-value hence reflects, in principle, the solubility of a detergent in water. Above the cmc-value, the concentration of solved detergent-monomers is constant.

The cmc-values of some detergents are described in the publication "Detergents: An Overview" J. M. Neugebauer in Methods in Enzymology 182 (1990), pages 239–253.

In this connection, it is particularly preferred if alkyl-phosphorylcholine with a chain length of C10–C16 is used as said second detergent. The inventors have recognized that, in particular with G-protein-coupled receptors, this detergent provides for a high yield of refolded protein.

According to own measurements of the inventors, the cmc-values for alkyl-phosphorylcholine with an alkyl rest of C12, C13, C14 or C16 are 500, 150, 50 or 5 $\mu$M.

In view of the fact that only few detergents are able at all to keep membrane proteins or even receptors stably in solution, it is the more surprising that alkyl-phosphorylcholine, the use of which for G-protein-coupled receptors has not yet been described in literature, is even able to induce a refolding into the native structure. In the case of an adenosine receptor, the inventors were able to prove that the refolded receptor has native binding properties if alkyl-phosphorylcholine is used as second detergent. Also for other receptors, the refolding could be shown with one of the detergents from the group mentioned above.

In this procedure, it is preferred if the protein is produced in form of inclusion bodies in a cell line transformed with an expression vector, which vector carries a gene coding for said protein, the protein being preferably part of a fusion protein and, before or after said exchange of detergents, is cleaved off from said fusion protein.

The expression of the DNA sequence coding for the protein according to the invention as fusion protein has, in comparison with the direct expression without carrier protein, the advantage that the carrier protein protects the protein which is desired, but, however, unknown to the expression system, against degradation by proteases and may result in a higher expression level. In particular by using glutathione-S-transferase (GST) as carrier protein, the solubility of proteins being expressed in large quantities is increased in the host cell and isolation is facilitated. The carrier protein can, further, be used for purifying fusion proteins, if suitable antibodies are provided. The same applies for purification methods with affinity chromatography.

In this method, it is further preferred if the inclusion bodies are purified and solubilized by adding the first detergent, wherein the first detergent is selected from the group:

N-Lauroylsarcosine, Dodecylsulfate, other charged detergents or urea or guanidiniumchloride in combination with charged or uncharged detergents.

It is important in this connection that the conditions to bring the protein in solution are denaturing, so that they do not allow a formulation of the native structure.

In this method, it is altogether preferred if the second detergent is present in a folding buffer with mixed lipid/detergent micelles, wherein the folding buffer contains preferably the second detergent and phospholipid from a natural source, preferably a lipid extract of tissue, in which the protein occurs naturally.

In this method, it is advantageous that, in comparison with the use of pure detergent micelles, the yield of native protein can even be improved. The lipid extract of the tissue, in which the receptor occurs naturally, can also be simulated by using lipids with a similar composition or by mixing same.

With reference to the exchange of detergents it is preferred, if same is done by a dialysis or ultrafiltration method or by chromatographic methods or by diluting said solubilized protein in a buffer which contains said second detergent.

The methods described insofar concerning the exchange of detergents are exchangeable amongst each other and offer, each for itself, specific advantages with reference to the handling, the duration of the method and the reachable yield.

After said exchange of detergents, at least one conserved disulfide bridge must be formed in the protein, preferably by adding a mixture of oxidized and reduced glutathione.

The folded protein can further be incorporated in proteoliposomes, which are artificially produced vesicles and represent a functional unit. With the help of these deliberately produced proteoliposomes, certain processes on the membrane proteins/receptors can be selectively investigated.

In view of the above, the present invention relates further to proteoliposomes with protein produced according to the method mentioned above.

Furthermore, the present invention relates to the use of a detergent for the production of proteins folded into their native or active structure of the kind described above, whereby the detergent is selected from the group:

Alkyl-N,N-dimethylglycine (alkyl=C8–C16)

Alkylglycosides (alkyl=C5–C12, also branched-chained or cyclic alkyl rests, glycoside=all mono- and disaccharides)

Saccharide fatty acid ester (e.g. sucrosemonododecanoate)

Alkylthioglycosides (alkyl=C5–C12, also branched-chained or cyclic alkyl rests, glycoside=all mono- and disaccharides with S- instead of O-glycosidic bond)

Bile acids (cholate, deoxycholate) and derivatives (e.g. CHAPS, CHAPSO)

Glucamides (MEGA-8 to -10, HEGA)

Lecithins and lysolecithins (e.g. DHPC, C12-lysolecithin)

Alkyl-Phosphorylcholine (Alkyl=C10–C16).

Further advantages can be taken from the following description of preferred embodiments.

It is to be understood that the features mentioned above and those yet to be explained below can be used not only in the respective combinations indicated, but also in other combinations or in isolation, without leaving the scope of the present invention.

The invention will be explained in more detail in the description below.

EXAMPLE 1

Production of an Expression Vector with cDNA for Receptor Protein

DNA sequences for several receptor proteins and also membrane proteins are in the EMBL database, in most cases, they do not have introns. With the help of primers, the required DNA can be produced via PCR from genomic DNA or via RT-PCR from mRNA.

This DNA is then cloned into an expression vector, which was constructed for the expression of a fusion protein. The carrier protein can be e.g. glutathione-S-transferase (GST), as described in the article by Kiefer et al. mentioned above, wherein a fusion protein was produced from the receptor OR5 and GST. The expression vector is transformed into a cell line which expresses the fusion protein. The protein is, in this procedure, not incorporated into the membrane, but exists at least partly aggregated in form of inclusion bodies in cytoplasm and is, thus, not correctly folded.

EXAMPLE 2

Isolation of Expressed Protein

The cDNA of one of the following receptors is, in-frame, inserted into the vector pGEX2a-c-His: AO adenosine receptor from the shark Squalus acanthias, human beta-2-adrenergic receptor, human neuropeptide YY1 receptor, human neuropeptide YY2 receptor, human melanocortine-1 receptor, human oxytocin receptor. This vector contains downstream of the Tac-promotor the sequence encoding glutathione-S-transferase and a subsequent thrombin cleavage site, followed by a polylinker sequence and, finally, six histidine codons and a stop codon.

The vectors are transformed into the E. coli strain BL21. The protein expression is induced by adding IPTG, and the cells are harvested after further three hours. After lysozyme treatment and homogenization by sonication, the membranes and inclusion bodies are separated from the soluble proteins by centrifugation.

EXAMPLE 3

Solubilization of the Protein and Detergent Exchange by Column Chromatographic The inclusion bodies are solubilized by adding 1.5% N-Lauroyl-sarcosine at 0° C. and diluted to fivefold volume with buffer (0.1% Alkyl(C14)phosphorylcholine). Thrombin is added to this solution and incubation is performed for 16 hours at 20° C. to separate the receptor from GST. After that, insoluble cell parts are isolated by centrifugation.

The supernatant is loaded onto Ni-NTA-Agarose (Qiagen) and incubated for one hour at 4° C., wherein the receptor binds to the nickel matrix. Thereafter, the nickel material is applied to a column and—to exchange detergent—washed with buffer, containing 0.01% Alkyl(C14)phosphorylcholine as second detergent. In that way, the N-Laurolylsarcosine (first detergent) and contaminating proteins are removed.

EXAMPLE 4

Reconstitution of the Protein

For the reconstitution, a lipid mixture consisting of 70% 1-Palmitoyl-2-oleoylphosphatidylcholine and 30% 1-Palmitoyl-2-oleoylphosphatidylglycerol is dissolved in chloroform together with the double (w:w) amount of dodecylmaltoside and the solvent is removed under vacuum. The purified protein obtained in example 3 is added and incubation is performed for at least one hour. The detergent is removed via a polystyrene column (Calbiosorb from Calbiochem), whereupon liposomes with incorporated receptor are formed (proteoliposomes).

By measuring ligand binding it could be shown that the receptor is present in native structure.

EXAMPLE 5

Detergent Exchange with Lipid/Detergent Micelles

The following stock solutions were prepared:

Cholesterol, Sigma C8667, 100 mg/ml in $CHCl_3$

Sheep brain phospholipid, Sigma P4264, 100 mg/ml in $CHCl_3$

Soybean lecithin, Sigma P3644, 100 mg/ml in $CHCl_3$ 100 mg of Alkyl(C16)-phosphorylcholine in 50 ml flasks, dissolved in 1–2 ml $CHCl_3$; adding 28 µg of cholesterol stock solution, 32 µl of sheep brain phospholipid stock solution, 40 µl of soybean lecithin stock solution; evaporation of $CHCl_3$ and drying for at least 30 minutes at less than 15 mbar; adding 1 ml of water to obtain a clear solution (detergent stock solution, 100 mg/ml)

thrombin, Sigma T4648, 1000 u/ml in $H_2O$, stored at −20° C.

sarcosyl: 10% N-Lauroylsarcosine in $H_2O$, autoclaved

10×PBS: 200 mM sodium phosphate, 1.5 M NaCl, pH 7.0

2 ml of 3% sarcosyl are resuspended in PBS and stored on ice. 2 ml of inclusion bodies obtained in example 2 are added and mixed and treated for one minute with sonication. Immediately afterwards, 16 ml of 0.1% detergent stock solution in PBS are added.

At this point already, an exchange of detergents takes place, sarcosyl is diluted below the cmc-value, while the end concentration of Alkyl(C16)phosphorylcholine is above the cmc-value.

After adding 15 u of thrombin, the solution is kept over night at 20° C. in order to cleave the fusion protein.

After that, the solution is centrifuged for 30 minutes at 4° C. with 40,000 rpm and the supernatant is removed.

To the supernatant, 20 mM imidazol of a 1 M stock solution (pH 7.0) are added. This solution is added to an appropriately equilibrated column resin Ni-NTA superflow (Qiagen) and is moderately rotated in a cold room (4–8° C.) for one hour to prevent the material from settling. In that way, the receptor protein binds to the column resin.

After that, the column resin is centrifuged for one minute at 2000 rpm, and the supernatant is removed to such an extent that the remaining supernatant corresponds to the bed volume. Ni-NTA agarose is taken up and loaded onto a column. At a flow rate of 2 ml/min, washing is performed with 40 ml of a 0.01% detergent stock solution in PBS, whereby a further exchange of detergents is performed with consideration of cmc-values.

The column is then eluted with 10 ml of PBS/0.01% detergent stock solution/0.3 M imidazole, and the fractions absorbing at 280 nm are collected.

Thereafter, a dialysis against 2 l of PBS is performed for four hours, as well as adding of 1 mM of GSH/0.1 mM GSSG from a 100× stock solution in water.

The solution is then stored for 48 hours at 4° C., whereupon, by flow dialysis, the adenosine binding was detectable, i.e. the receptor was present in native form.

EXAMPLE 6

Refolding of the beta-2-adrenergic Receptor by Exchange of Detergents without Purification of the Protein The inclusion bodies including beta-2-adrenergic receptor obtained in example 2 are solubilized by adding 1.5%. N-Lauroyl-sarcosine at 0° C. and diluted with the tenfold volume of a solution of 0.1% Dodecyl—·—D-maltoside in 20 mM Na-Malonate buffer pH 6.0. After that, thrombin (50 units per milligram protein) is added and incubated for one hour at 20° C. After centrifugation, the supernatant is applied to a lipid film as in example 4 and the protein is reconstituted in proteoliposomes.

By measuring the binding of a fluorescent ligand of the beta-adrenergic receptor (BODIPY-TMR-CGP 12177 by Molecular Probes) the successful refolding is shown.

What is claimed is:

1. A method for production of proteins folded into their native or active structure, said proteins being from the family of G-protein-coupled receptors, comprising:
    providing a protein from the family of G-protein-coupled receptors solubilized in a first detergent, and
    exchanging said first detergent for a second detergent, to induce folding of said protein in its native or active form, wherein said second detergent is selected from the group consisting of:
        alkylglycosides, comprising unbranched, branched or cyclic C5–C12 alkyl chain; and glycoside, selected from the group consisting of monosaccharides and disaccharides; and
        alkyl-phosphorylcholine with chain length of C10–C16.

2. The method of claim 1, wherein said second detergent is provided in a folding buffer with mixed lipid/detergent micelles.

3. The method of claim 2, wherein said folding buffer contains said second detergent and phospholipid from a natural source.

4. The method of claim 1, wherein said exchange of detergents is done by a dialysis- or ultrafiltration method.

5. The method of claim 1, wherein said exchange of detergents is carried out via a chromatographic method.

6. The method of claim 1, wherein said exchange of detergents is carried out by diluting said solubilized protein in a buffer which contains said second detergent.

7. The method of claim 1, wherein after said exchange of detergents at least one disulfide bridge is formed in said protein.

8. The method of claim 1, wherein said folded protein is incorporated in proteoliposomes.

9. The method of claim 1, wherein said protein is produced as inclusion bodies in a cell line transformed with an expression vector which carries a gene coding for said protein.

10. The method of claim 1, wherein said protein is part of a fusion protein and is cleaved off from said fusion protein.

11. The method of claim 9, further comprising
    purifying said inclusion bodies and,
    solubilizing said purified inclusion bodies by adding said first detergent.

12. The method of claim 1, wherein said first detergent is selected from the group N-Lauroylsarcosine, dodecylsulfate, other charged detergents or urea or guanidiniumchloride in combination with charged or uncharged detergents.

13. The method of claim 1, wherein said second detergent has a concentration that is above its critical miceller concentration.

14. The method of claim 1, wherein said second detergent is alkyl-phosphorylcholine with a chain length of C10–C16.

15. The method of claim 3, wherein said phospholipid is a lipid extract of tissue in which said protein occurs naturally.

16. The method of claim 7, where the disulfide bridge is formed by adding a mixture of oxidized and reduced glutathione.

17. The method of claim 11, wherein said second detergent is alkyl-phosphorylcholine with a chain length of C10–C16.

18. The method of claim 12, wherein said second detergent is alkyl-phosphorylcholine with a chain length of C10–C16.

19. The method of claim 13, wherein said second detergent is alkyl-phosphorylcholine with a chain length of C10–C16.

* * * * *